United States Patent [19]

Heidenreich et al.

[11] Patent Number: 4,962,019

[45] Date of Patent: Oct. 9, 1990

[54] INDICATORS FOR THE DETECTION OF THIOL GROUPS

[75] Inventors: Holger Heidenreich, Cologne; Klaus Wehling, Wuppertal, both of Fed. Rep. of Germany

[73] Assignee: Miles Inc., Elkhart, Ind.

[21] Appl. No.: 481,618

[22] Filed: Feb. 20, 1990

Related U.S. Application Data

[60] Division of Ser. No. 432,466, Nov. 7, 1989, Pat. No. 4,931,579, which is a continuation-in-part of Ser. No. 105,565, Oct. 8, 1987, abandoned.

[30] Foreign Application Priority Data

Oct. 10, 1986 [DE] Fed. Rep. of Germany ........ 3634525

[51] Int. Cl.$^5$ ..................... C12Q 1/25; C07C 311/17
[52] U.S. Cl. ........................... 435/4; 435/187; 435/195; 435/183; 544/159; 544/383; 546/236; 548/379; 548/579; 558/390; 562/430; 564/83
[58] Field of Search ................. 564/83; 435/183, 187, 435/195, 4

[56] References Cited

U.S. PATENT DOCUMENTS 4,615,972 10/1985 Gallacher ............................. 435/4

FOREIGN PATENT DOCUMENTS

| 3614432 | 11/1987 | Fed. Rep. of Germany | ...... 435/195 |
| 3634525 | 4/1988 | Fed. Rep. of Germany | .......... 435/4 |
| 0029184 | 8/1974 | Japan | .................................... 564/83 |
| 6108759 | 8/1981 | Japan | .................................... 564/83 |
| 2269684 | 11/1987 | Japan | ................................. 435/183 |
| 2269685 | 11/1987 | Japan | ................................. 435/183 |

Primary Examiner—Glennon H. Hollrah
Assistant Examiner—Susan P. Treanor
Attorney, Agent, or Firm—Roger N. Coe

[57] ABSTRACT

Indicators for the detection of thio groups are disclosed together with processes for the preparation of such indicators. The indicators of the invention contain compounds having the following general formula

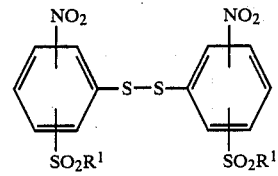

5 Claims, No Drawings

INDICATORS FOR THE DETECTION OF THIOL GROUPS

RELATED APPLICATION

This is a division of application Ser. No. 432,466, filed on Nov. 7, 1989, now U.S. Pat. No. 4,931,579, which is a continuation-in-part of U.S. Ser. No. 105,565, filed 10/8/87, now abandoned.

FIELD OF THE INVENTION

The invention relates to indicators for the detection of thiol groups which are present in a system or are formed in a step prior to the detection reaction. Processes for the preparation of the indicators are also described.

Thiol groups can be formed by chemical reactions, such as, for example, reduction of disulphides, or biochemical reactions. The preferred biochemical reactions which lead to the formation of thiol groups are illustrated by the following equation:

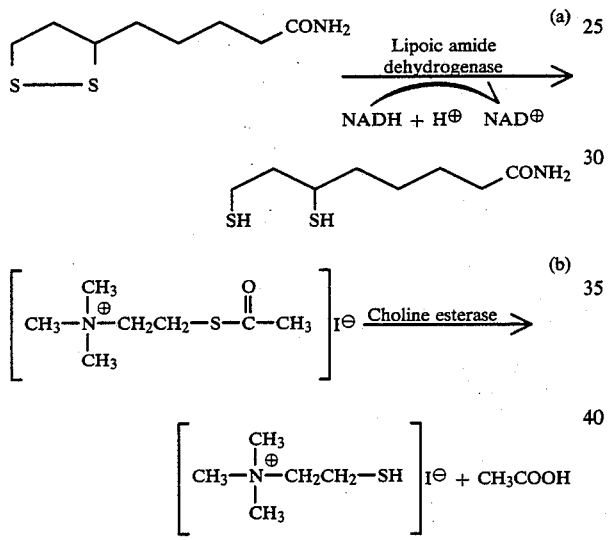

BACKGROUND OF THE INVENTION

Numerous methods are known for the detection of compounds containing thiol groups. A method which is mentioned particularly frequently is that described by G. L. Ellman in *Arch. Biochem. Biophys.*, 82:70–77 (1959). The described method is based on the formation of the yellow anion of 3-mercapto-6-nitro-benzoic acid formed by reaction between a thiol and 3,3'-dithio-bis-6-nitro-benzoic acid (Ellman's reagent).

The reaction is sensitive and fast. However, the anion of Ellman's reagent is very sensitive towards oxidation and the coloration formed is therefore unstable. Furthermore, Ellman's reagent is very sparingly soluble in polar solvents, such as, for example, water and, therefore, can be used to only a limited degree for some thiol solutions, especially those which are prepared biochemically in aqueous systems.

SUMMARY OF THE INVENTION

The compounds according to the invention have the general formula I

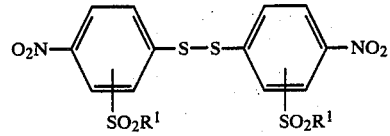

wherein

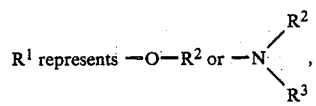

and $R^2$ and $R^3$ independently of one another represent $C_1$–$C_4$-alkyl, which can be substituted by halogen, —COOH, cyano, $C_1$–$C_4$-alkoxy, hydroxyl, —O-$SO_3H$, —$SO_3H$ or amino, it being possible for the amino group in turn to be substituted by $C_1$–$C_4$-alkyl which is optionally substituted by halogen, hydroxyl, cyano, —$OSO_3H$ or —$SO_3H$, or by phenyl or benzyl groups; or $R^2$ and $R^3$, together with the N atom, represent a pyrrolidine, pyrazoline, piperidine, piperazine or morpholine ring, which can be substituted by $C_1$– to $C_4$-alkyl or phenyl; $R^3$ can also be hydrogen.

Compounds which are of special interest are those of the general formula II

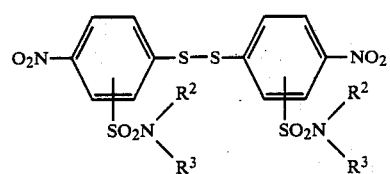

wherein $R^2$ and $R^3$ have the meaning given above, except $R^2$ and $R^3$ may both be hydrogen.

Especially preferred compounds are those of the general formula III

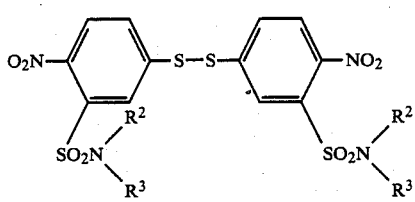

wherein $R^2$ and $R^3$ have the meaning described in the case of formula II.

The compounds of the invention are prepared by processes which have known individual steps. In particular, a chloro-nitro-benzenesulphonyl chloride of the formula

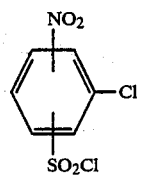

can be converted with an amine or alcoholate of the formula H-R¹, wherein R¹ has the above-mentioned meaning, into the corresponding chloro-nitro-benzene-sulphonic acid derivative. A chloride/sulphide replacement reaction is then carried out in the presence of Na₂S, followed by oxidation, a symmetric disulphide being obtained.

The following equation shows the route of the synthesis:

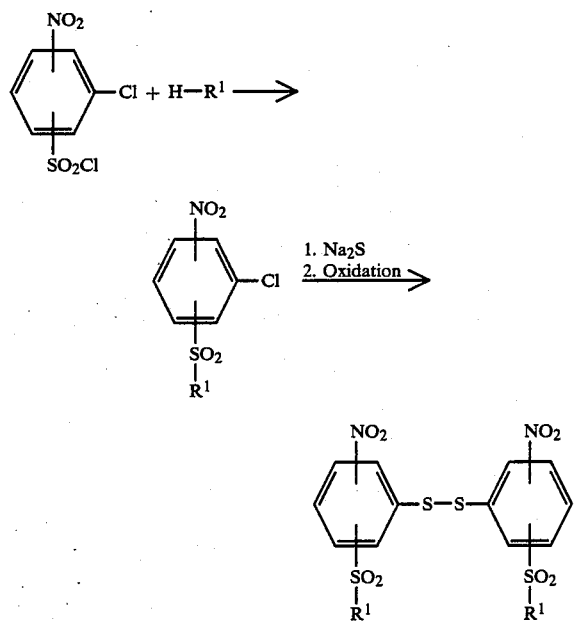

The compounds of the invention are particularly suitable for use as indicators in test agents for thiols or thiol precursors, such as, for example, lipoic amide, gluthathione or coenzyme A. Compounds of the present invention are up to 50 times less sensitive to ascorbic acid interference compared to Ellman type compounds. Moreover, as acknowledged by Ellman in *Arch. Biochem. Biophys.*, 82:70-77 (1959), the Ellman compounds are very sensitive towards oxidation and very sparsely soluble in polar solvents. Accordingly, these indicators have limited utility, particularly in biochemical determinations which involve aqueous systems.

Test agents or test systems, in the context of the present invention, are to be understood as those which can be measured in a cell. In addition to the compounds of the general formula (I), the test agents contain all the reagents necessary for the determination of the particular analysis substance, such as enzymes, substrates, coenzymes, effectors, antigens, antibodies and the like. These test agents can furthermore also contain nonreacting substances, such as, for example, buffers, wetting agents and stabilizers Enzymes which form thiol groups and which may be mentioned are thioglycosidases, thioether hydrolases and also esterases, such as, for example, choline esterase. There may also be mentioned enzymes which form thiol groups with the aid of NADH and NADPH as the coenzyme, such as lipoic amide dehydrogenase and gluthathione reductase. The enzymes last mentioned can be used in test systems in which NADH or NADPH is formed. Such reactions are the known dehydrogenase-catalyzed oxidations of substrates.

From the reagents and substances mentioned, it is possible to prepare reagent combinations which are mixed as a solution powder or are in the form of tablets or a lyophilizate. The reagent combination (if it is not already present as a solution) is taken up in water or another suitable solvent and a reagent solution is prepared. If the reagent combination consists of individual components, these are mixed with one another. After mixing the sample (for example, substrate solution, enzyme solution, blood, serum, plasma or urine) with an aliquot portion of the reagent mixture, the resulting color is measured on a photometer and the particular concentration or substrate concentration is calculated via the molar extinction coefficients and the volumes of reagent and sample added. Both kinetic and end point measurements are possible.

The compounds of the general formula (I) can also be impregnated, together with the reagent or reagents necessary for the particular parameter detection or other enzymes and the buffer system, if appropriate wetting agents and activators as well as other auxiliaries dissolve. Absorbent or swellable carriers, preferably filter paper or absorbent nonwoven glass or plastic, are impregnated or sprayed with these solutions. The system is then dried. The reagent carriers thus prepared can be used either as rapid diagnostics for direct determination of the contents of liquids (for example in body fluids, such as blood, urine or saliva, or in food stuffs, for example fruit juices, milk or the like). The liquid is thereby applied directly to the reagent carrier or this is immersed briefly in the liquid. Semiquantitative determination is possible by allocating to the resulting color a comparison color. Quantitative evaluation can be carried out by reflectance photometry.

It is also possible to introduce the compounds of the general formula (I) into carrier matrices which have been prepared from casting solutions. Cellulose, cellulose derivatives, gelatin, gelatin derivatives or even plastics, such as polyurethanes and acrylamide, are examples. It is advantageous if the compounds of the general formula (I) and, if appropriate, the other reagents required are added directly to the casting solution, whereupon it is possible for the test device, consisting of carrier and reagents, to be produced in one operation.

A reagent solution with which substrates or enzymes can be determination in a cell using a photometer as described above can be prepared by eluting the above-mentioned reagents from the absorbent carrier with water or a buffer or serum.

Suitable buffers for the test agents mentioned are phosphate, citrate, borate and buffers with alkali metal or ammonium counterions. However, other systems can also be used. pH values should be 6 to 10; in particular 6.5 to 7.5.

Wetting agents are, in particular, anionic and cationic wetting agents which undergo ionic interactions with the compounds according to the invention. However, nonionic wetting agents which activate the enzymes can also be used. Sodium lauryl-sulphate, dioctyl sodium sulphosuccinate and alkylaryl polyether-alcohols are preferred.

Effectors which can be employed are those known for particular enzymatic reactions. Other auxiliaries which can be employed are customary thickeners, solubilizing agents, emulsifiers, optical brighteners, contrast agents and the like, such as are known in corresponding tests with other chromogens.

EXAMPLE 1

130 grams (g) of the sodium salt of 2-chloro-5nitro-benzenesulphonic acid are added to a solution of 120 g of sodium sulphide 0.9H$_2$O in 750 milliliters (ml) of water. The mixture is stirred at room temperature for 10 hours and the solution is acidified. The hydrogen sulphide formed is removed with the aid of nitrogen. A pH value of 10 is then established with sodium hydroxide solution and the oxidation is carried out with 125 g of iodine to give the disulphide. During the addition of iodine, the pH value must be continuously adjusted with sodium hydroxide solution. When the oxidation has ended, a pH value of 7.5 is established and the following compound is salted out with 20% of sodium chloride.

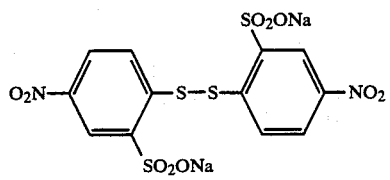

EXAMPLE 2

101 g of 3,4-dinitro-chlorobenezene are heated under reflux in a solution of 500 ml of water and 126 g of sodium sulphite for 30 hours. The mixture is allowed to cool and the yellow precipitate which has separated out, of the following formula, is recrystallized from water.

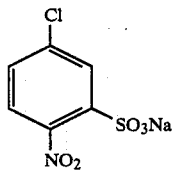

25.9 g of the sodium 3-chloro-6-nitro-benzenesulphonate prepared above are added to a solution of 25.0 g of sodium sulphide 0.9H$_2$O in 250 ml of water at room temperature. After a reaction time of 5 hours (thin layer chromatography control), the solution is acidified, the hydrogen sulphide which has formed is removed with nitrogen and the solution is then clarified over active charcoal The yellow filtrate, containing the mercapto compound of the following structure

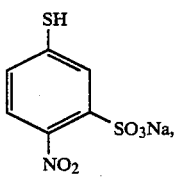

is then brought to pH 10 with sodium hydroxide solution and oxidized with 25 g of iodine. The pH value is maintained during the oxidation by addition of sodium hydroxide solution. The disulphide formed is salted out with sodium chloride and recrystallized from water. It is characterized by the following $^{13}$C-NMR spectrum. $^{13}$C shifts in DMSO-D$_6$

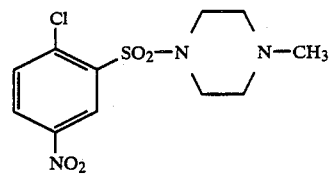

| C atoms | δ [ppm] |
| --- | --- |
| C-1/C-1' | 138.300 |
| C-2/C-2' | 126.478 |
| C-3/C-3' | 140.481 |
| C-4/C-4' | 127.248 |
| C-5/C-5' | 123.948 |
| C-6/C-6' | 146.616 |

EXAMPLE 3

50.0 g of N-methyl-piperazine are dissolved in 300 ml of chloroform. After addition of 69 ml of triethylamine, 128 g of 2-chloro-5-nitrobenzenesulphonyl chloride are introduced at room temperature. After 5 hours, the mixture was poured onto ice and the sulphonamide formed, of the following formula, is extracted with chloroform.

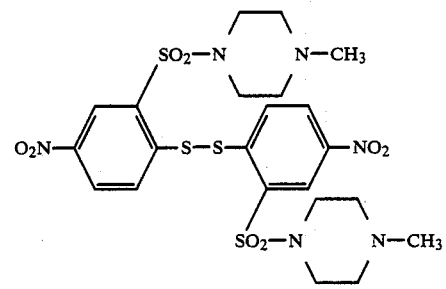

A freshly prepared sodium disulphide solution obtained from 48.0 g of sodium sulphide 0.9H$_2$O in 250 ml of ethanol with 6.4 g of sulphur is added dropwise to a solution of 63.9 g of the nitro compound prepared above in 300 ml of ethanol. The mixture is boiled under a reflux condenser for 2 hours and is then poured into 1 (liter) of ice-water. The pale yellow product which precipitates is filtered off with suction and crystallized from ethanol to give the following material having a melting point of 205° C.

EXAMPLE 4

25.9 g of the sodium salt of 3-chloro-6-nitrobenzenesulphonic acid are added in portions to a mixture of 50 ml of phosphorus oxychloride and 25 g of phosphorus pentachloride at 80° C. After 2 hours, the evolution of HCl has subsided The solution is concentrated on a rotary evaporator, the residue is taken up in toluene, the toluene phase is washed with ice-water and the extract is dried and evaporated again on a rotary evaporator. The sulphochloride of the following formula remains a pale crystalline mass.

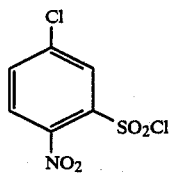

25.6 g of 3-chloro-6-nitrobenzenesulphonyl chloride, dissolved in 100 ml of chloroform, are added dropwise to 250 ml of chloroform containing a mixture of 10.0 g of N-methylpiperazine and 11 ml of triethylamine at room temperature. When the reaction has ended, the mixture is poured onto ice and extracted with chloroform and the following sulphonamide is thus isolated.

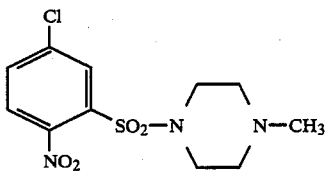

31.95 g of the sulphonamide prepared above are then added to a suspension of 25.0 g of sodium sulphide 0.9H$_2$O in 100 ml of dimethylformamide at room temperature. After 1 hour, the chloride/sulphide replacement reaction has ended. The reaction mixture is poured onto ice, acidified and filtered with suction. 27.3 g of the following mercapto compound are obtained.

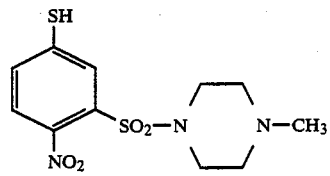

15.85 g of the mercapto compound prepared above are dissolved in a mixture of 200 ml of ethanol and 50 ml of triethylamine and 12.5 g of iodine are then added in portions. The end of the reaction is indicated by the change in color from red-brown to yellow. The reaction product is poured onto ice and the pale yellow precipitate is filtered off with suction. The disulphide of the following structure, recrystallized from chloroform/ethanol, melts from 173° C. (decomposition).

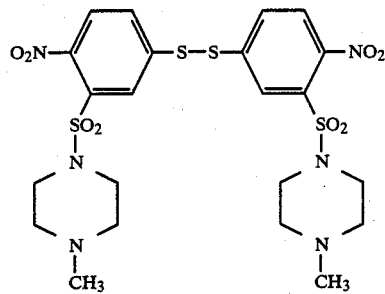

The following disulphides have been prepared by the methods described in Examples 1 to 4.

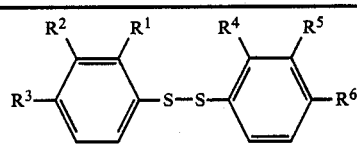

| Example | R$^1$ | R$^2$ | R$^3$ | R$^4$ | R$^5$ | R$^6$ |
|---|---|---|---|---|---|---|
| 5 | H | SO$_2$N(CH$_3$)CH$_3$ | NO$_2$ | H | SO$_2$N(CH$_3$)CH$_3$ | NO$_2$ |
| 6 | H | SO$_2$NHCH$_2$COOH | NO$_2$ | H | SO$_2$NHCH$_2$COOH | NO$_2$ |
| 7 | H | SO$_2$N(C$_2$H$_4$OSO$_3$H)C$_2$H$_5$ | NO$_2$ | H | SO$_2$N(C$_2$H$_4$OSO$_3$H)C$_2$H$_5$ | NO$_2$ |
| 8 | H | SO$_2$N(CH$_3$)C$_2$H$_4$SO$_3$H | NO$_2$ | H | SO$_2$N(CH$_3$)C$_2$H$_4$SO$_3$H | NO$_2$ |
| 9 | SO$_2$N(C$_2$H$_5$)C$_2$H$_5$ | H | NO$_2$ | SO$_2$N(C$_2$H$_5$)C$_2$H$_5$ | H | NO$_2$ |

-continued $$R^3 \underset{R^2}{\overset{R^1}{\diagdown}} \text{—S—S—} \underset{R^5}{\overset{R^4}{\diagdown}} R^6$$

| Example | R¹ | R² | R³ | R⁴ | R⁵ | R⁶ |
|---|---|---|---|---|---|---|
| 10 | SO₂N(CH₃)(CH₂CH₂SO₃H) | H | NO₂ | SO₂N(CH₃)(CH₂CH₂SO₃H) | H | NO₂ |
| 11 | SO₂—O—C₆H₅ | H | NO₂ | SO₂—O—C₆H₅ | H | NO₂ |
| 12 | H | SO₂—O—C₆H₅ | NO₂ | H | SO₂—O—C₆H₅ | NO₂ |
| 13 | H | SO₂—O—C₄H₉ | NO₂ | H | SO₂—O—C₄H₉ | NO₂ |
| 14 | H | SO₂N(C₂H₄OH)(C₂H₅) | NO₂ | H | SO₂N(C₂H₄OH)(C₂H₅) | NO₂ |
| 15 | H | SO₂N(C₂H₄OSO₃H)₂ | NO₂ | H | SO₂N(C₂H₄OSO₃H)₂ | NO₂ |
| 16 | H | SO₂NHC₂H₄SO₃H | NO₂ | H | SO₂NHC₂H₄SO₃H | NO₂ |
| 17 | SO₂NCH₂CH₂N(CH₃)₂ (H) | H | NO₂ | SO₂NCH₂CH₂N(CH₃)₂ (H) | H | NO₂ |
| 18 | H | SO₂NH—CH₂CH₂CH₂—N(CH₃)₂ | NO₂ | H | SO₂NH—CH₂CH₂CH₂—N(CH₃)₂ | NO₂ |
| 19 | SO₂N(morpholino) | H | NO₂ | SO₂N(morpholino) | H | NO₂ |
| 20 | SO₂N(C₄H₉)₂ | H | NO₂ | SO₂N(C₄H₉)₂ | H | NO₂ |

EXAMPLE 21

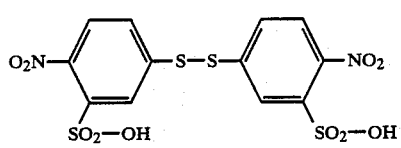

To test the compound from Example 2 as an indicator for NADH in the test system described, the compound was dissolved in water to give a 20 mM (millimolar) solution. The following reagent constituents were pipetted into a cell together: 1,810 microliters (μl) of buffer (0.1 M/1 of Tris amine buffer, pH 7), 100 μl of the compound from Example 2 (20 mmol/1 in H₂O), 50 μl of lipoic amide (50 mmol/1) and 20 μl of lipoic amide dehydrogenase (1,200 kU/1).

After measurement of the reagent blank value, the reaction was started by addition of 20 μl of NADH. The extinction maximum measured is ar 400 nanometers (nm). Kinetic investigation showed a stable end point (change in extinction within 20 minutes <1%) after a reaction of time of only 1 minute.

To test for functionality and linearity, NADH concentrations in the range from 1 to 10 mmol/1 were measured in the test mixture. The extinction differences measured at 400 nm (nanometers) are summarized in Table 1.

TABLE 1

| NADH (mmol/l) | Compound from Example 37 pH 7 | | | Comparison DTNB (Ellman) pH 7.5 | | |
|---|---|---|---|---|---|---|
| | $E_1$ | $E_2$ | $\Delta E_{400\,nm}$ | $E_1$ | $E_2$ | $\Delta E_{430\,nm}$ |
| 1 | 0.391 | 0.529 | 0.138 | 0.159 | 0.348 | 0.189 |
| 2 | 0.382 | 0.663 | 0.281 | 0.160 | 0.553 | 0.393 |
| 3 | 0.384 | 0.813 | 0.429 | 0.158 | 0.755 | 0.597 |
| 4 | 0.381 | 0.957 | 0.576 | 0.159 | 0.958 | 0.799 |
| 5 | 0.382 | 1.104 | 0.722 | 0.159 | 1.153 | 0.994 |
| 6 | 0.382 | 1.244 | 0.862 | 0.158 | 1.359 | 1.201 |
| 7 | 0.382 | 1.389 | 1.007 | 0.157 | 1.550 | 1.393 |
| 8 | 0.383 | 1.536 | 1.153 | 0.157 | 1.765 | 1.608 |
| 9 | 0.383 | 1.676 | 1.293 | 0.158 | 1.956 | 1.798 |
| 10 | 0.384 | 1.792 | 1.498 | 0.160 | 2.104 | 1.944 |

Table 2 shows the results of the test for interference by ascorbic acid. For this test, 20 μl of an NADH solution (5 mmol/1) and also 20 μl of an ascorbic acid solution of 1 mmol/1 are added to the above mixture and the resulting extinctions are measured.

TABLE 2

| | $E_1$ | $E_2$ | $\Delta E_{400\,nm}$ | |
|---|---|---|---|---|
| without ascorbic acid | | | | |
| | 0.379 | 1.089 | 0.710 | |
| | 0.386 | 1.097 | 0.711 | |
| | 0.383 | 1.093 | 0.710 | $\bar{x} = 0.710$ |
| with ascorbic acid | | | | |
| | 0.383 | 1.089 | 0.706 | |
| | 0.381 | 1.088 | 0.707 | |
| | 0.384 | 1.087 | 0.703 | $\bar{x} = 0.705$ |

The values measured in the absence of ascorbic acid are on average 0.7% above the values measured in the presence of ascorbic acid. The present test is not influenced by ascorbic acid.

EXAMPLE 22

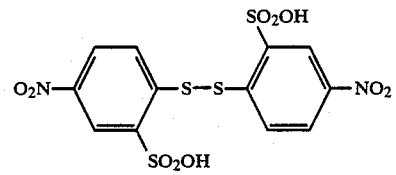

For the testing of the compound from Example 1, the same reaction conditions as in Example 21 were chosen. However, 0.1 M Tris pH 9 was chosen as the buffer, since a faster reaction (end point within 1 minute) was achieved with this substance at pH 9 than at pH 7.

The absorption maximum measured is at 425 nm. The coloration is stable within the period measured (20 minutes). Table 3 shows the function and linearity testing after addition of NADH concentrations in the range from 1 to 10 mmol/1.

TABLE 3

| NADH (mmol/l) | Compound from Example 38 pH 9 | | | Comparison DTNB (Ellman) pH 7.5 | | |
|---|---|---|---|---|---|---|
| | $E_1$ | $E_2$ | $\Delta E_{425\,nm}$ | $E_1$ | $E_2$ | $\Delta E_{430\,nm}$ |
| 1 | 0.154 | 0.404 | 0.250 | 0.159 | 0.348 | 0.189 |
| 2 | 0.150 | 0.663 | 0.513 | 0.160 | 0.553 | 0.393 |
| 3 | 0.147 | 0.914 | 0.767 | 0.158 | 0.755 | 0.597 |
| 4 | 0.148 | 1.185 | 1.037 | 0.159 | 0.958 | 0.799 |
| 5 | 0.149 | 1.452 | 1.303 | 0.159 | 1.153 | 0.994 |
| 6 | 0.148 | 1.696 | 1.548 | 0.158 | 1.359 | 1.201 |
| 7 | 0.151 | 1.970 | 1.819 | 0.157 | 1.550 | 1.393 |
| 8 | 0.158 | 2.220 | 2.062 | 0.157 | 1.765 | 1.608 |

TABLE 3-continued

| NADH (mmol/l) | Compound from Example 38 pH 9 | | | Comparison DTNB (Ellman) pH 7.5 | | |
|---|---|---|---|---|---|---|
| | $E_1$ | $E_2$ | $\Delta E_{425\,nm}$ | $E_1$ | $E_2$ | $\Delta E_{430\,nm}$ |
| 9 | 0.158 | 2.420 | 2.270 | 0.158 | 1.956 | 1.798 |
| 10 | 0.146 | 2.655 | 2.509 | 0.160 | 2.104 | 1.944 |

Ascorbate sensitivity was determined between the compound of this example and the Ellman reagent which has the structure:

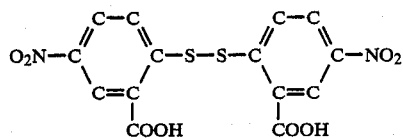

Based on kinetic data the signal with the Ellman compound was lowered by ascorbic acid by an amount of 5.3% whereas the compound of the present invention was lowered only 0.1%. In other words, the Ellman compound is over 50 times more sensitive to ascorbate acid compared to the compound of the present invention.

Similarly, when the compound having the following structure was employed the signal obtained was lowered only 0.1% by ascorbic acid.

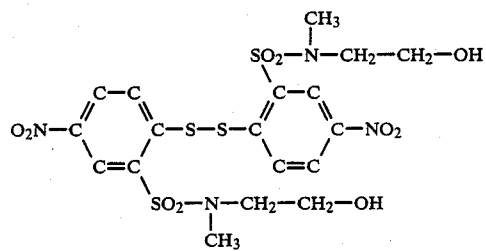

Again, the Ellman compound is over 50 times more sensitive to ascorbate acid.

Yet another compound of the claimed invention, a compound having the formula

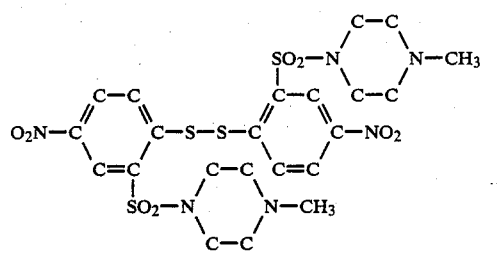

had its signal lowered by ascorbic acid only 0.9%.

EXAMPLE 23

To determine the extinction maxima, further compounds were dissolved in dimethylformamide and in each case 2 ml of 0.1 M/1 Tris buffer pH 9 and 10 μl of mercaptoethanol were added to 50 μl of the solution. The extinction maxima are shown in Table 4.

TABLE 4

|  | Extinction Maximum |
| --- | --- |
| Example 9 | 445 nm |
| Example 19 | 420 nm |
| Example 20 | 464 nm |

Obviously, many other modifications and variations of the invention as hereinbefore set forth can be made without departing from the spirit and scope thereof.

What is claimed is:

1. The compound having the general formula

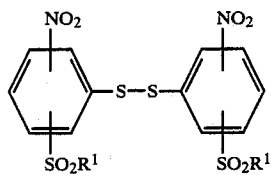

wherein

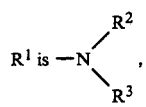

and

R² is C₁–C₄-alkyl; C₁–C₄ alkyl substituted by halogen, C₁–C₄-alkoxy, hydroxyl, —OSO₃H, —SO₃H, amino, or amino substituted by C₁–C₄-alkyl;

wherein the C₁–C₄ alkyl maybe substituted by halogen, hydroxyl, —OSO₃H, —SO₃H, phenyl or a benzyl group;

R³ is hydrogen or R².

2. The compound of claim 1 having the formula

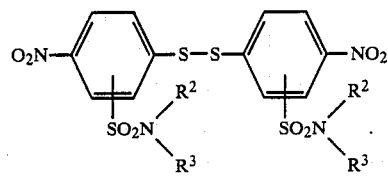

3. The compound of claim 1 having the formula

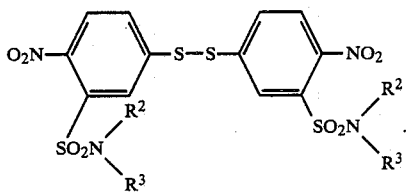

4. A test agent having as an indicator a compound of claim 1 in combination with an enzyme.

5. A method of using the test agent according to claim 4 for the detection of thiol groups.

* * * * *